United States Patent
Milo (10) Patent No.: US 10,049,769 B2
(45) Date of Patent: Aug. 14, 2018

(54) CLINICAL COMPONENT ROUTING SYSTEM

(71) Applicant: Children's Hospital Medical Center of Akron, Akron, OH (US)

(72) Inventor: Anton G. C. Milo, Akron, OH (US)

(73) Assignee: CHILDREN'S HOSPITAL MEDICAL CENTER OF AKRON, Akron, OH (US)

( * ) Notice: Subject to any disclaimer, the term of this patent is extended or adjusted under 35 U.S.C. 154(b) by 195 days.

(21) Appl. No.: 14/859,649

(22) Filed: Sep. 21, 2015

(65) Prior Publication Data
US 2016/0085933 A1    Mar. 24, 2016

Related U.S. Application Data

(60) Provisional application No. 62/052,775, filed on Sep. 19, 2014.

(51) Int. Cl.
*G16H 40/63*    (2018.01)

(52) U.S. Cl.
CPC .................. *G16H 40/63* (2018.01)

(58) Field of Classification Search
CPC ............... G06F 13/4081; A61B 5/742; A61B 2562/221–2562/228
See application file for complete search history.

(56) References Cited

U.S. PATENT DOCUMENTS

| | | | | |
|---|---|---|---|---|
| 5,836,453 A | * | 11/1998 | Herrera ............... | A61G 7/0503 206/702 |
| 6,202,360 B1 | * | 3/2001 | Rattner ................ | A61B 50/10 312/209 |
| 6,402,546 B1 | | 7/2002 | Groves et al. | |
| 6,743,046 B2 | * | 6/2004 | Rus .................... | H01R 13/5224 248/274.1 |
| 7,119,279 B2 | * | 10/2006 | Niehaus .............. | H02G 3/0487 138/128 |

(Continued)

OTHER PUBLICATIONS

Maguire Enterprises, Inc., OR Boom Cabling System for routing analog ECG and IBP signals through the operating room booms, 2 pages.

(Continued)

*Primary Examiner* — Brian T Misiura
(74) *Attorney, Agent, or Firm* — Tucker Ellis LLP; Heather M. Barnes; Michael G. Craig (57) ABSTRACT

One or more techniques and/or systems are disclosed for a system that may be used for managing routing of clinical operation component lines. A first communication coupling component can selectably receive a first connector that is engaged with a first communication bus connected to a first part of a first clinical operation component. A second communication coupling component can selectably receive a second connector that is engaged with a second communication bus connected to a second part of the first clinical operation component. A bus routing component is connected to the first receptacle and the second receptacle, and the bus routing component comprises a third communication bus that is used to communicatively couple the first connector and the second connector, resulting in communicatively coupling the second part with the first part of the first clinical operation component.

18 Claims, 7 Drawing Sheets

(56) References Cited

U.S. PATENT DOCUMENTS

| | | |
|---|---|---|
| 8,255,026 B1 | 8/2012 | Al-Ali |
| 8,315,683 B2 | 11/2012 | Al-Ali et al. |
| 8,905,585 B2 * | 12/2014 | Dallam ................ A61B 90/35 362/227 |
| 8,909,320 B2 * | 12/2014 | Jenkins ............... A61B 5/0002 5/600 |
| 9,106,038 B2 * | 8/2015 | Telfort ............... A61B 5/04282 |
| 9,549,687 B2 * | 1/2017 | Georgiev ............. A61B 5/0555 |
| 9,582,055 B2 * | 2/2017 | De Jong ................ A61B 8/565 |
| 9,606,601 B2 * | 3/2017 | Spencer ................. G06F 1/266 |
| 2003/0008550 A1 | 1/2003 | Tse et al. |
| 2005/0098345 A1 | 5/2005 | Niehaus et al. |
| 2008/0071153 A1 | 3/2008 | Al-Ali et al. |
| 2008/0203066 A1 | 8/2008 | Feldhausen et al. |
| 2009/0173846 A1 * | 7/2009 | Katz ...................... A61B 90/50 248/124.1 |
| 2009/0299157 A1 | 12/2009 | Telfort et al. |
| 2010/0274338 A1 | 10/2010 | Ollivier |
| 2011/0152628 A1 | 6/2011 | Balji et al. |
| 2012/0211319 A1 | 8/2012 | Jacobi et al. |
| 2014/0037105 A1 | 2/2014 | Heineman |

OTHER PUBLICATIONS

PCT International Search Report and Written Opinion from International Application No. PCT/US2015/051147, dated Dec. 22, 2015, 12 pages.

European Patent Office, Extended European Search Report for 15842950.6, dated May 18, 2018, Munich, 13 pages.

Best Sellers in Cable Sleeves | Amazon Best Sellers Web Page, https://web.archive.org/web/20131028183353/https://www.amazon.com/Best-Sellers-Electronics-Cable-Sleeves/zgbs/electronics/6577542011, dated Apr. 5, 2018, pp. 1-6.

Selector Switch Boxes: Electronics | Amazon Web Page, https://web.archive.org/web/20140910165858/http://www.Amazon.com/B?IE=utf8&NODE=172546, dated Apr. 5, 2018, pp. 1-4.

* cited by examiner

CLINICAL COMPONENT ROUTING SYSTEM

CROSS-REFERENCE TO RELATED APPLICATIONS

This application claims priority to Provisional Patent Application U.S. Ser. No. 62/052,775, entitled CLINICAL COMPONENT ROUTING SYSTEM, filed Sep. 19, 2014, which is incorporated herein by reference.

BACKGROUND

In a clinical operation environment, such as an operating theater, examination room, patient room, etc., clinicians often use clinical operation systems, such as monitors, anesthesia machines, suction devices and other systems, to monitor patient vitals, perform operational procedures, etc. Typically, respective clinical operation systems have communication bus lines, such as cables, tubes, cords, power lines, etc., that run between a base component and a remote tool, such as a sensor. As an example, these communication lines can provide a logistical problem for placement of devices and routing of the lines, as well as providing a potential safety and operational hazard.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

As provided herein, a system may be devised that allows one or more communication bus lines to be effectively routed (e.g., together) in a manner that mitigates potential safety concerns in a clinical operation environment, such as trip hazards, loss of connections, and/or confined operation space. As an example, one or more communication bus lines, which run between a monitoring component and a sensor component, can be connected to a device at a first end, and connected to the device at a second end, where the device effectively routes the bus line(s) in a desired position, such as one that provides improved safety, operational and space use considerations.

In one implementation, a device for use in managing routing of a clinical operation component line can comprise a first communication coupling component that may be configured to selectably receive a first connector engaged with a first communication bus, which is engaged with a first part of a first clinical operation component. Further, the device can comprise a second communication coupling component that is configured to selectably receive a second connector, which is engaged with a second communication bus engaged with a second part of the first clinical operation component, where the second part is configured to communicate with the first part. Additionally, the device can comprise a bus routing component that is sealably coupled with the first receptacle and the second receptacle, where the bus routing component comprises a third communication bus that is configured to communicatively couple with the first connector and the second connector.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein.

DETAILED DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices may be shown in block diagram form in order to facilitate describing the claimed subject matter.

In one aspect, a system and device can be devised that may communicatively couple a first component of a clinical system with a second component of a clinical system. As an example, in a clinical operating theatre environment, one or more sensors may be used to monitor a patient's vital life functions, such as heart rate and rhythm, breathing, blood pressure, body temperature, pulse oxygen, body fluid balance, etc., as well as monitoring other systems such as administered gas mixtures, fluids, medicines, etc. In this example, a sensor may be communicatively coupled with a monitoring device or system, such as through a communication bus (e.g., cable, cord, line, hose, tube, etc.), which may be used by an attending clinician to monitor a patient. In one implementation, a device may communicatively couple with the first component of the clinical system (e.g., the monitor), and communicatively couple with the second component of the clinical system (e.g., the sensor), and the device may be used to route the communication bus between the first and second components.

Figure 1:
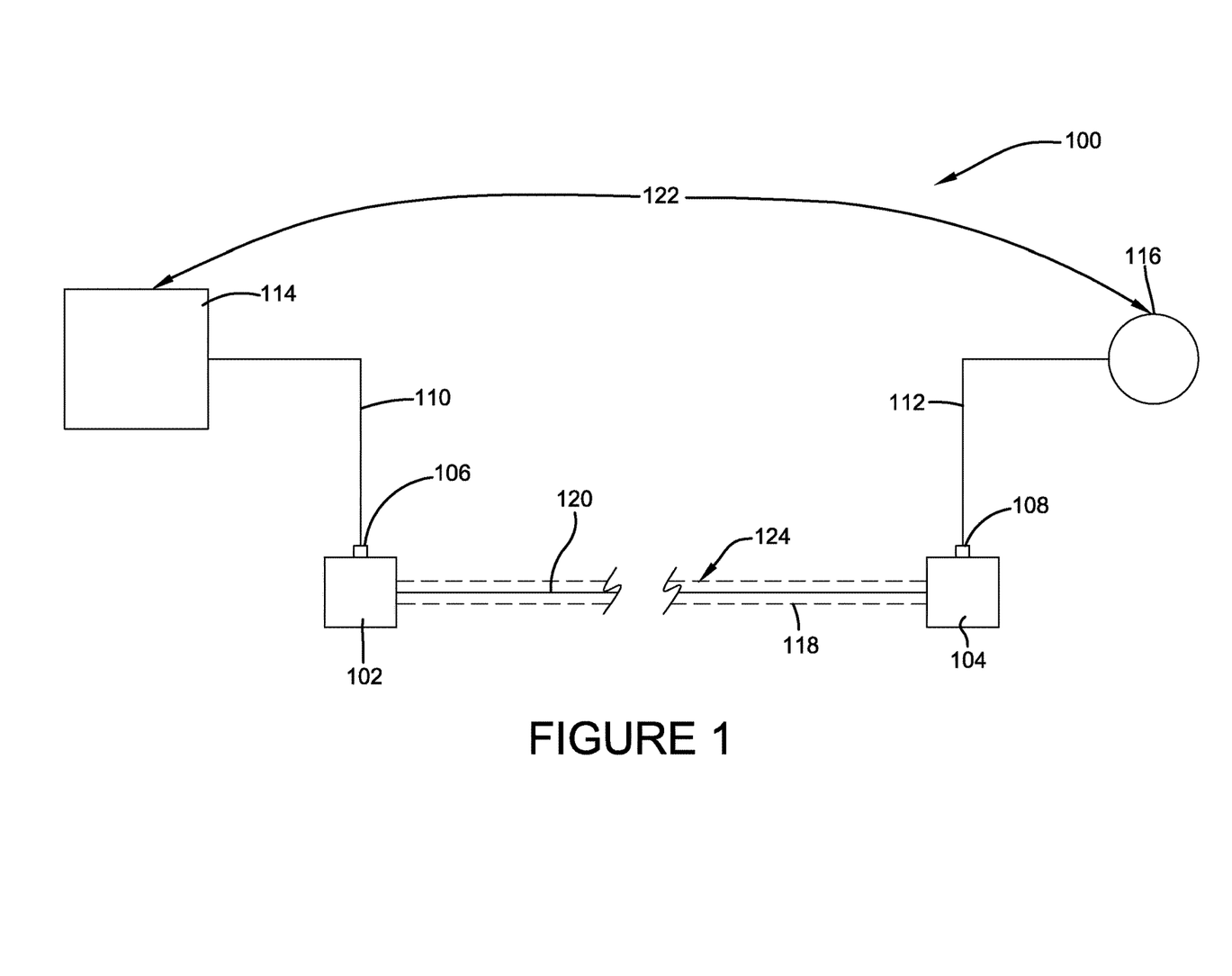
FIG. 1 is a schematic diagram illustrating an exemplary implementation of a clinical component routing system.

FIG. 1 is a schematic diagram illustrating an exemplary implementation 100 of a clinical component routing system. In the exemplary implementation 100, a first communication coupling component, such as a first receptacle 102, may be configured to selectably receive a first connector 106. The first connector 106 may be engaged with a first communication bus 110 that may be engaged with a first part 114 of a first clinical operation component 122. Further, as illustrated in the exemplary implementation 100, a second communication coupling component, such as a second receptacle 104, may be configured to selectably receive a second connector 108. The second connector 108 may be engaged with a second communication bus 112 that may be engaged with a second part 116 of the first clinical operation component 122.

In the exemplary implementation 100, a bus routing component, such as a routing sleeve or routing member 118, may be sealably coupled with the first receptacle 102 and the second receptacle 104. Further, the routing sleeve 118 can comprise a flexible portion (e.g., entirely or partially flexible), and can comprise a flexible outer covering and an inner chamber 124. The inner chamber 124 can comprise at least one routing communications bus, such as a third communication bus 120 (e.g., a routing communication bus), that may be configured to communicatively couple with the first connector 106 and the second connector 108 (e.g., when coupled with the respective receptacles). In this implementation 100, the second part 116 of the first clinical operation component 122 may be configured to communicate with the first part 114 of the first clinical operation component 122. For example, data generated by the second part 116 of the first clinical operation component 122 can be communicatively transmitted to the first part 114 of the first clinical operation component 122 by way of the second communication bus 112, the second connector 108, the third communication bus 120, the first connector 106, and the first communication bus 110.

As an example, in one implementation, a first clinical operation component (e.g., 122) may comprise a patient vital sign monitor (e.g., heart rate, blood pressure, etc.), which can comprise a sensor (e.g., disposed in the second part 116) engaged with the patient, and a monitoring component (e.g., disposed in the first part 114). In this example, a communication cable from the monitor (e.g., first communication bus 110) may couple with the first receptacle (e.g., 102) using the first connector (e.g., 106) connected to an end of the communication cable from the monitor. Further, the communication cable from the sensor (e.g., the second communication bus 112) may couple with the second receptacle (e.g., 104) using the second connector (e.g., 108). In this way, for example, the sensor may communicate with monitor using a cable (e.g., the third communication bus 120 inside the flexible sleeve 118). As an example, using the communication bus in the sleeve may allow for loose cables to be appropriately secured in a desired configuration, thereby mitigating trip hazards, damage to equipment, dislodging sensors or cables from systems, etc., and potentially providing a more efficient work space for clinicians.

Figure 2A:
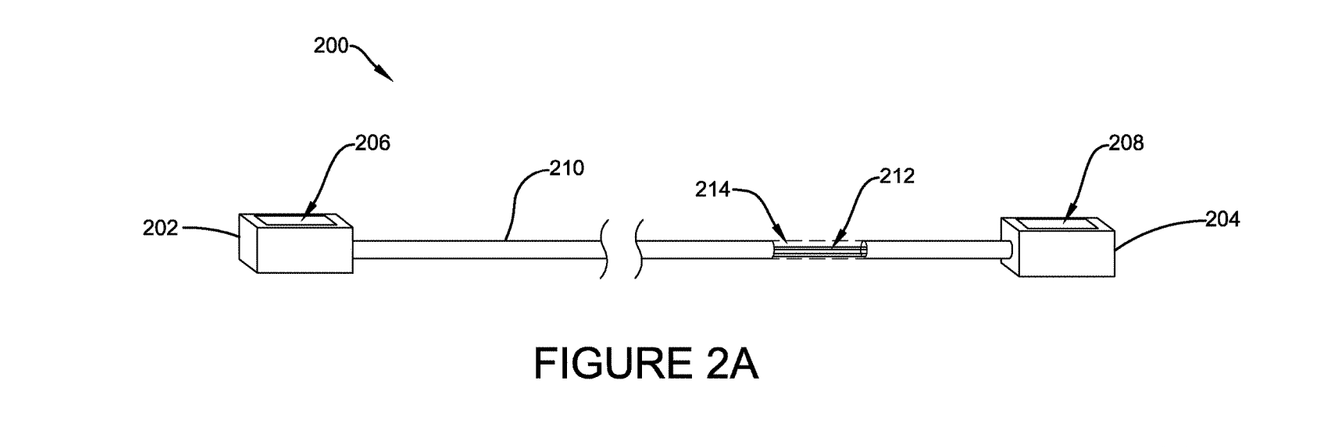
FIGS. 2A and 2B are component diagrams illustrating exemplary implementations of one or more portions of one or more systems described herein.
Figure 2B:
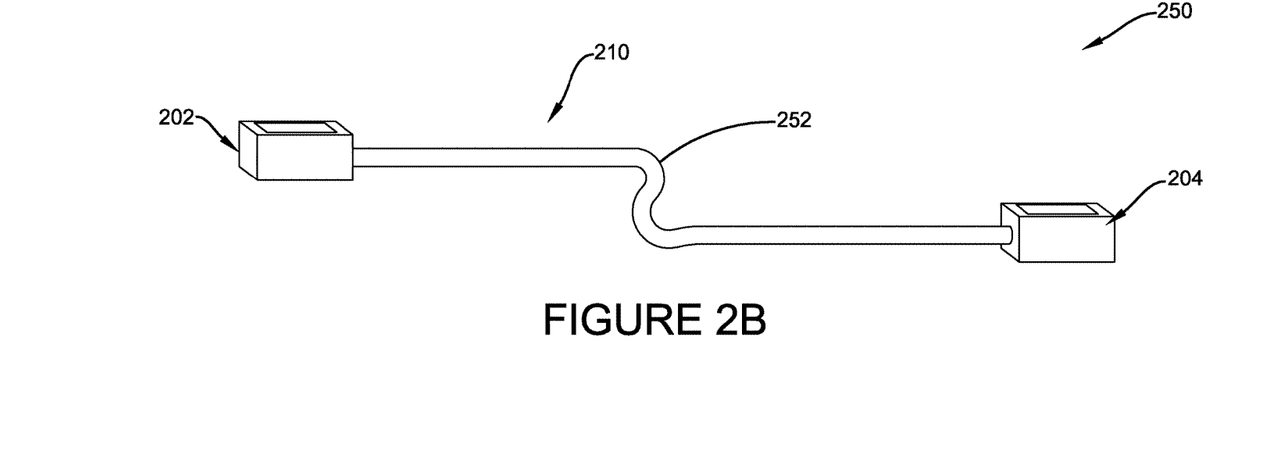

FIGS. 2A and 2B are component diagrams illustrating exemplary implementations 200, 250 of a clinical component routing system. In this implementation 200, the first receptacle 202 and second receptacle 204 may respectively comprise a container (e.g., of any shape or size) that may be configured to receive respective ends of one or more communication cables 212 that are disposed in an inner chamber 214 of the bus routing component 210. It will be appreciated that the sleeve 210 (e.g., and consequently the communication bus(ses) 212) may comprise any suitable length, for example, where the length may be suitable for the clinical environment, clinical system used, and/or procedure being performed. Further, in one implementation 250, the bus routing component 210 may comprise a flexible sleeve portion 252. For example, the flexible sleeve portion 252 may allow the sleeve (e.g., and communication bus(ses)) to be routed in a non-linear manner (e.g., around an object, or at another angle).

Figure 3A:
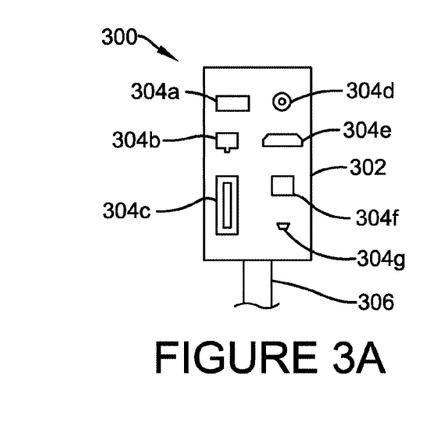
FIGS. 3A, 3B, 3C, and 3D are component diagrams illustrating exemplary implementations of one or more portions of one or more systems described herein.
Figure 3B:
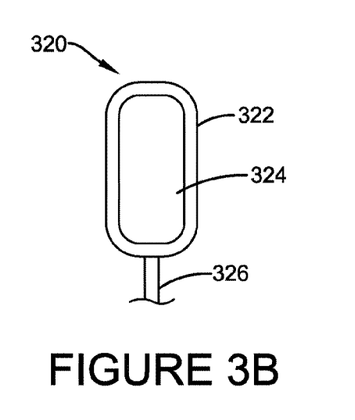

Additionally, in this implementation 200, the first receptacle 202 can comprise a first connector receiver 206, and the second receptacle 204 can comprise a second connector receiver 208. As an illustrative example, as illustrated in FIGS. 3A-3D, the first connector receiver 206 and/or the second connector receiver 208 may comprise a variety of configurations and may comprise one or more connection ports (e.g., a first connection port, a second connection port, etc.), which may be chosen based on expected use and/or sound engineering principles. In FIG. 3A, in one example implementation 300, the connector receiver portion of the receptacle 302 can comprise one or more connection ports 304a, 304b, 304c, 304d, 304e, 304f, 304g. For example, the receptacle can comprise one or more of a same type of connection port, and/or a variety of different port configurations.

In this implementation 300, the connection ports 304 may comprise one or more configurations, for example, configured to receive a particular connector (e.g., 106, 108 of FIG. 1) that may be used with a particular clinical operation system (e.g., 122 of FIG. 1). In one implementation, the connector may be associated with a particular type of clinical monitoring equipment, for example, and may be proprietary to a particular manufacturer or equipment type (e.g., anesthesia monitoring systems); or may comprise a non-proprietary connector used by more than one type of equipment or by more than one manufacturer (e.g., USB type, HDMI, etc.). As one example, a first patient monitoring system may utilize a first type of connector that merely fits with a first type of connection port 304a, and a second patient monitoring system may utilize a second type of connector that merely fits with a second type of connection port 304b (e.g., and a third type 304c, fourth type 304d, etc. (304e, 304f, 304g)).

As an example, potential connectors used by the connection ports may comprise: RF coaxial cable connectors, which can comprise SMA, N type, TNC, FME, SMC, MCX, BNC, SMB, Mini UHF, and UHF; RCA connectors, which are generally used for audio, composite and component cables; mini-DIN connectors, which are cylindrical in shape and feature between three and nine pins, each compatible with various audio and/or visual devices; VGA connectors, which feature three rows of five pins each, with two screws on each end to hold the connector into the unit; HDMI connectors, which are used for cables combining an uncompressed digital video signal with an uncompressed digital audio signal; the F-connector, which is a type of radio frequency connector commonly used for cable television, antenna and satellite connections; common computer-related data connectors, which can include USB, DVI and IEEE 1394 (also called FireWire) connectors; as well as other types network connectors (e.g., universal connector, GE connector, Ohmeda (H), Datex (N), Masimo LNC and LNCS, DIN types (3 through 17 pin, and more), mini snap, DVB, BD, Edward, Abbot, Binder, Redel, Lemo, Banana, etc.); just to name a few.

FIGS. 3A, 3B, 3C, and 3D illustrate example implementations 300, 320, 340, 360 of configurations of a receptacle (e.g., 102, 104 of FIG. 1). The example implementation 300 comprises a rectangular-shaped, box-like receptacle 302, having the connection ports 304 disposed on a top-side of the receptacle 302. Further, in this implementation 300, a sleeve 306 may be engaged at a side portion of the receptacle 302. The example implementation 320 comprises a rounded, box-like receptacle 322, having a connector receiver 324 disposed on a top-portion. In this implementation 320, the sleeve 326 may be engaged at a side wall portion of the receptacle 322.

Figure 3C:
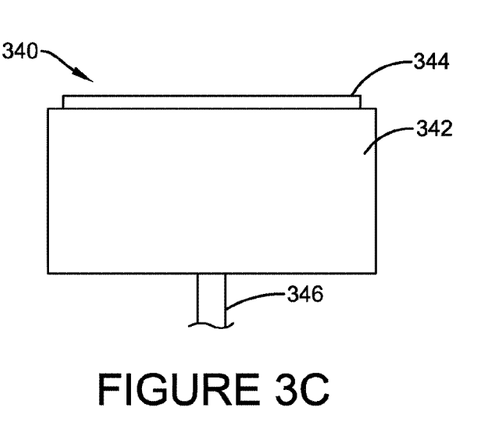

In another example implementation 340, the connector receiver 344 can be disposed on the top wall of the receptacle 342, while the sleeve 346 may be engaged at a bottom wall of the receptacle. Further, the sleeve may be sealably engaged with the corresponding receptacle, for example, such that fluids are mitigated from entry into the sleeve and/or receptacle. It will be appreciated that the receptacle, connector receiver, sleeve configuration and arrangement is not limited to those implementation described herein. It is anticipated that those skilled in the art may devise alternate arrangements and configuration, shapes and sizes of the various components. For example, the receptacle shape and size, the connector receiver location, and the sleeve placement may be dictated by the type of clinical environment, equipment and systems used, and other factors, including, but not limited to sound engineering principles.

Figure 3D:
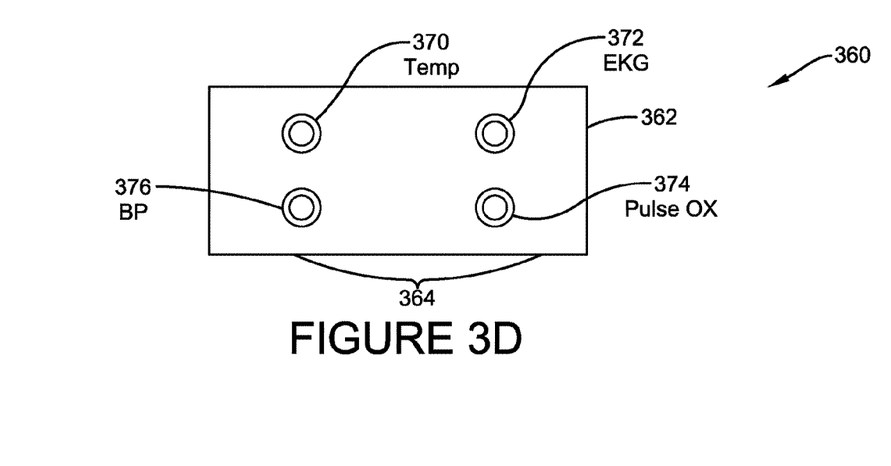

FIG. 3D illustrates an exemplary implementation 360 of a receptacle 362. In this implementation 360, the connector receiver 364 comprises a plurality of connector ports 370, 372, 374, 376, respectively comprising a similar shape and size (e.g., although various port configurations, shapes and/or sizes are anticipated). In this implementation, a first port 370 may be configured to communicatively couple with a body temperature monitoring system; a second port 372 may be configured to communicatively couple with an electrocardiogram monitoring system; a third port 374 may be configured to communicatively couple with a pulse blood oxygen monitoring system; and a fourth port 376 may be configured to communicatively couple with a blood pressure monitoring system. Further, in one implementation, the first receptacle (e.g., 362) may comprise the configuration of the receptacle in implementation 360, and a second receptacle may comprise a similar arrangement.

That is, for example, the communication bus from the monitor to the first receptacle may have a similar connection as the communication bus between the sensor and the second receptacle. In this way, for example, a clinical operation system may have one or more monitors that connect respective communication bus lines to the first receptacle, and the second receptacle may connect corresponding communication bus lines to the corresponding sensors (e.g., engaged with the patient). In this example, the sleeve can comprise four communication bus lines, each connecting between corresponding connectors at the first and second receptacles. In other implementations, an example sleeve (e.g., 118 of FIG. 1, 210 of FIG. 2, etc.) can comprise one or a plurality of communication bus lines, respectively connecting between corresponding connectors at the first and second receptacles. It is anticipated that those skilled in the art may devise alternate arrangements and configuration, numbers, and types of the various lines. For example, the number, size and type of line in the sleeve may be dictated by the type of clinical environment, equipment and systems used, and other factors, including, but not limited to sound engineering principles.

Figure 4:
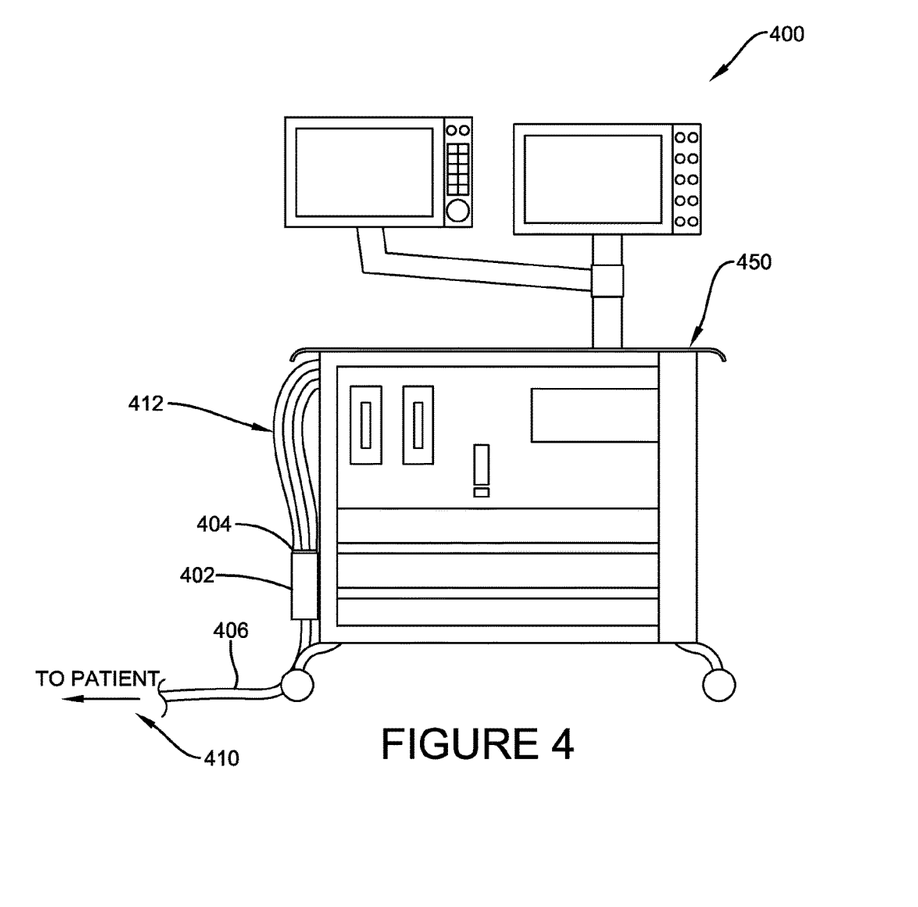
FIG. 4 is a component diagram illustrating an exemplary environment where one or more portions of one or more systems described herein may be implemented.

FIG. 4 is a component diagram illustrating an example implementation 400 of a portion of the one or more systems described herein. In this implementation 400, a clinical operation system 450 (e.g., an anesthesia machine) may comprise a plurality of communication bus lines 412 (e.g., sensor signal cables) that are communicatively coupled to one or more monitoring components in the system 450. A connector (e.g., 106 of FIG. 1) for the respective communication bus lines 412 can be coupled with a corresponding connector port (e.g. 304 of FIG. 3A, 370, 372, 374, 376 of FIG. 3D) disposed on a connector receiver 404 engaged with a first receptacle 402. Further, in this implementation 400, the first receptacle 402 may be selectably (e.g., or fixedly) engaged with at least a portion of the clinical operation system 450. A sleeve 406, comprising a plurality of connector bus lines, may be engaged with the first receptacle 402. The sleeve 406 may be selectably directed from the clinical operation system 450 toward the patient 410 (e.g., in a manner that mitigates disruption, and/or improves efficiency, of the clinical operations).

Figure 5:
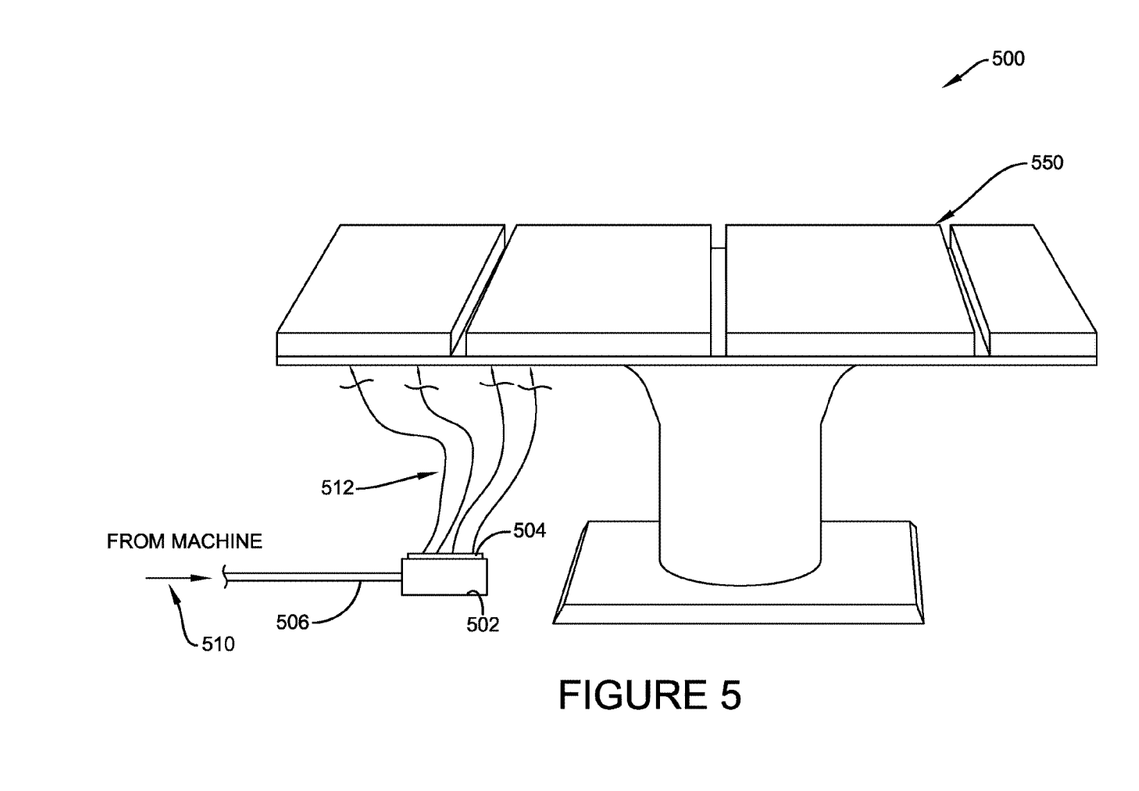
FIG. 5 is a component diagram illustrating an exemplary environment where one or more portions of one or more systems described herein may be implemented.

FIG. 5 is a component diagram illustrating an example implementation 500 of a portion of the one or more systems described herein. In this implementation 500, the sleeve 506, comprising the respective connector bus lines, can be selectably directed from the first portion of the clinical operation system 510 toward a clinical operation station 550 (e.g., operating table, bed, or examination table, patient cart). A second receptacle 502 can be engaged with the sleeve 506, and the connector bus lines disposed in the sleeve 506 may be engaged with one or more corresponding connector ports disposed on a second connector receiver 504 engaged with the second receptacle 502. Further, corresponding second communication bus lines 512 can be connected to the corresponding ports, and the respective second communication bus lines 512 may be engaged with corresponding sensors (e.g., appropriately engaged with the patient). In this way, for example, sensor data generated by the respective sensors can be transmitted through the second communication bus lines 512, through the corresponding connector bus lines in the sleeve 506, to the first receptacle (e.g., 402 of FIG. 4), which may be in communicative coupling with the first portion of the clinical operation system (e.g., 450 of FIG. 4).

Figure 6:
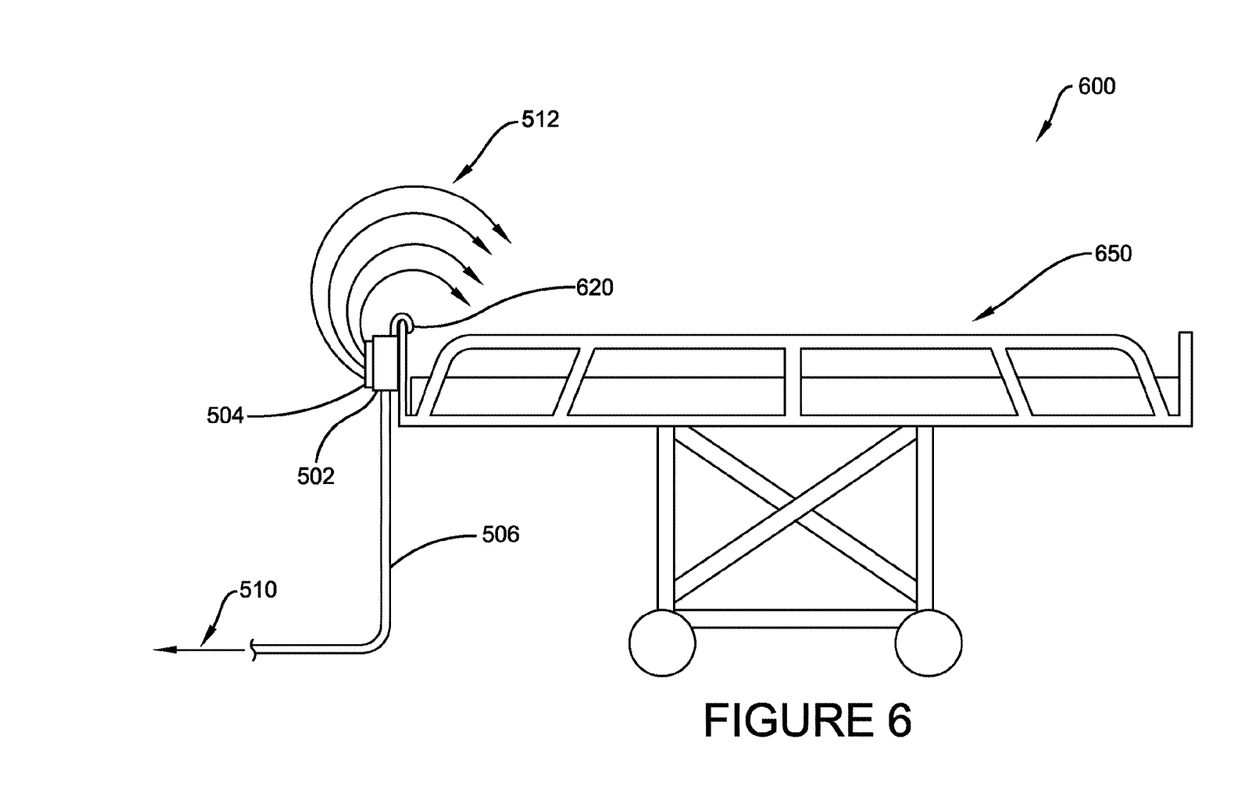
FIG. 6 is a component diagram illustrating an exemplary environment where one or more portions of one or more systems described herein may be implemented.

FIG. 6 is a component diagram illustrating an example of an alternate implementation 600 of the one or more systems described herein. In this implementation 600, the second receptacle 502 may be selectably engaged with the clinical operation station 650 (e.g., patient bed, gurney, table, cart, etc.). In one implementation, a station engagement means 620 (e.g., a station engagement component, such as a hook, fastener, clip, etc.) may be engaged with the second receptacle 502, and may be configured to selectably engage the station 650, for example, such that the second receptacle 502 can be coupled with or removed from the station 650 as appropriate.

Figure 7:
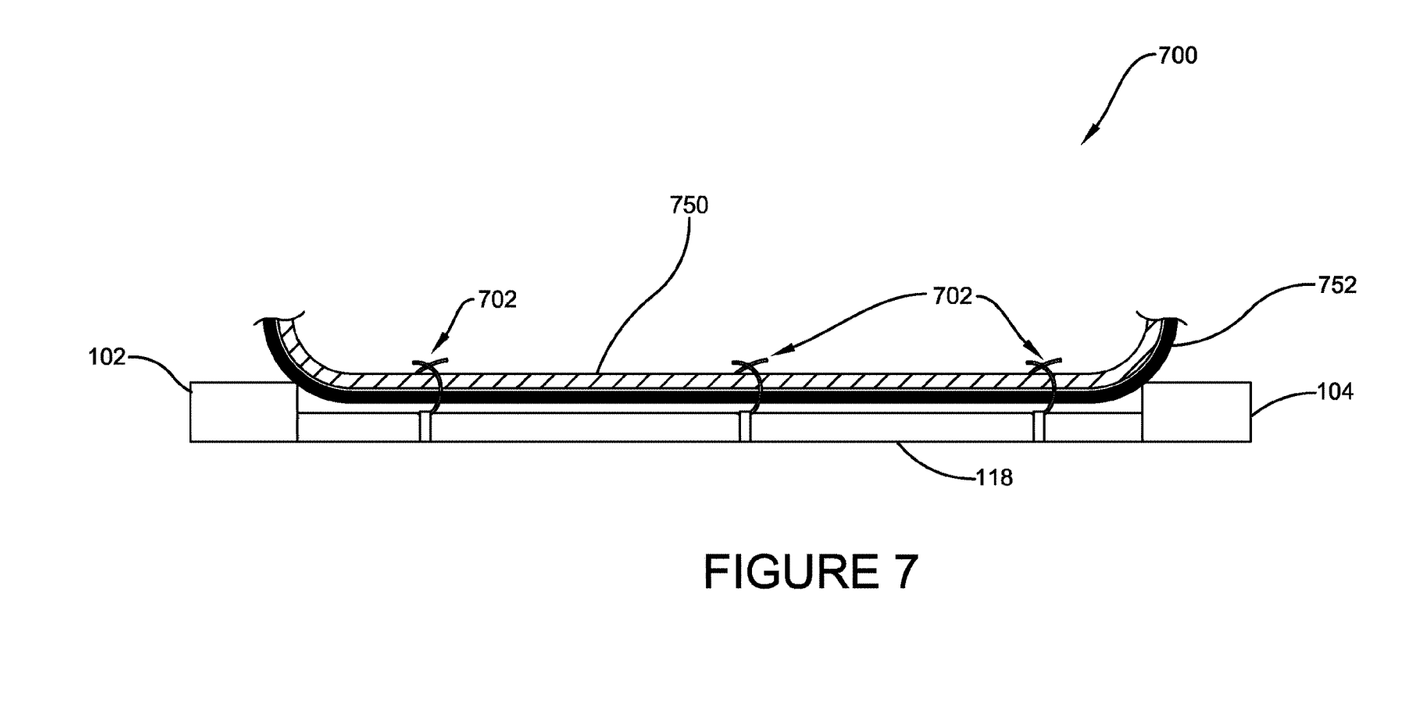
FIG. 7 is a component diagram illustrating an exemplary implementation of one or more portions of one or more systems described herein.

FIG. 7 is a component diagram illustrating an example implementation 700 of one or more portions of one or more systems described herein. In this implementation 700, one or more component retention holders 702 can be disposed on the outer surface of the sleeve 118. The one or more component retention holders 702 can be configured to selectably retain a portion of a clinical operation component, such as a cord, cable, data bus, and/or tube. As an example, a second (e.g., and third, fourth, etc.) clinical operation component may comprise a communication bus that is not configured to couple with a port disposed on the first and/or second receptacle (e.g., 102, 104 of FIG. 1); or where more clinical operation components are being utilized than ports are available on the respective receptacles. In this example, the communication bus from the second clinical operation component may be selectably retained on the sleeve 118 by way of the one or more component retention holders 702. In one or more implementations, the component retention holders 702 may comprise a clip, fastener, clamp, and/or a device that allows the communication bus of the second (e.g., and third, fourth, etc.) clinical operation component to be effectively, selectably retained on the sleeve 118.

As an illustrative example, an anesthesia machine may comprise a suction tube 750 that can be used at the patient station (e.g., 650 of FIG. 6); and/or another device used at the patient station may utilize a power cord 752 that is plugged into a remote power supply. In this example, the suction tube 750 and/or the power cord 752 (e.g., and other communication bus lines from other systems) can be effectively retained on the sleeve 118 by way of the one or more component retention holders 702. In this way, a plurality of communication bus lines may effectively be bundled together in or on the flexible sleeve, and the sleeve may be routed appropriately to mitigate potential safety concerns, and/or improve efficiency, in the clinical operation environment (e.g., operating theater).

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A device for use in managing routing of a clinical operation component line, comprising:
    a first receptacle configured to selectably receive a first connector engaged with a first communication bus engaged with a first part of a first clinical operation component, the first connector selectably engaged with an anesthesia machine;
    a second receptacle configured to selectably receive a second connector engaged with a second communication bus engaged with a second part of the first clinical operation component, the second part of the first clinical operation component configured to communicate with the first part of the first clinical operation component; and
    a routing member having an outer surface and an inner chamber, the routing member coupled with the first receptacle and the second receptacle, and comprising a third communication bus disposed inside the inner chamber of the routing member and configured to communicatively couple with the first connector and the second connector,
    a suction tube retained on the outer surface of the routing member;
    the second receptacle configured to be selectably engaged with one or more of:
        a patient bed;
        a clinical table; and
        a patient cart.

2. The device of claim 1, the first receptacle comprising a first connection port configured to receive the first connector, the first connection port communicatively coupled with the third communication bus.

3. The device of claim 2, the second receptacle comprising a second connection port configured to receive the second connector, the second connection port communicatively coupled with the third communication bus.

4. The device of claim 1, the first receptacle comprising a plurality of connection ports respectively configured to receive a corresponding connector, and respectively communicatively coupled with a corresponding communication bus disposed in the routing member.

5. The device of claim 4, the second receptacle comprising a plurality of connection ports respectively configured to receive a corresponding connector, and respectively communicatively coupled with a corresponding communication bus disposed in the routing member, the corresponding connectors being one or more of a RF coaxial cable connector, a RCA connector, a mini-DIN connector, a VGA connector, a HDMI connector, a F-connector, USB, DVI and IEEE 1394 connector, and network connectors.

6. The device of claim 1, the routing member comprising a flexible portion configured to be routed in a non-linear manner.

7. The device of claim 1, comprising one or more component retention holders, disposed on the outer surface of the routing member, and configured to selectably retain the suction tube and one or more of a cord, cable, bus, and tube from a second clinical operation component in engagement with the routing member.

8. The device of claim 1, the first receptacle configured to be selectably engaged with at least a portion of the first clinical operation component.

9. The device of claim 1, the first part comprising a monitoring device, and the second part comprising a patient sensor configured to provide data to the monitoring device.

10. A system for managing routing of a clinical operation component line, comprising:
 a first communication coupling component, configured to selectably, communicatively couple with a first part of a clinical operation component, the first connector selectably engaged with an anesthesia machine;
 a second communication coupling component, configured to selectably, communicatively couple with a second part of the clinical operation component, the second communication coupling component configured to be selectably engaged with one or more of:
 a patient bed;
 a clinical table; and
 a patient cart;
 a bus routing component, sealably engaged with the first communication coupling component and the second communication coupling component, the bus routing component comprising:
 a flexible outer covering; and
 an inner chamber configured to at least partially enclose and route a routing communication bus between the first communication coupling component and the second communication coupling component to communicatively couple the first part of a clinical operation component with the second part of the clinical operation component;
 a suction tube retained on the outer covering of the routing member.

11. The system of claim 10, the first communication coupling component comprising a first connection port configured to receive a first connector communicatively coupled with the first part of the clinical operation component, the first connection port communicatively coupled with the routing communication bus.

12. The system of claim 11, the second communication coupling component comprising a second connection port configured to receive a second connector communicatively coupled with the second part of the clinical operation component, the second connection port communicatively coupled with the routing communication bus.

13. The system of claim 12, the first communication coupling component comprising a plurality of connection ports respectively configured to receive a corresponding connector coupled with the first part of the clinical operation component, and respectively communicatively coupled with a corresponding routing communication bus disposed in the routing component, the corresponding connectors being one or more of a RF coaxial cable connector, a RCA connector, a mini-DIN connector, a VGA connector, a HDMI connector, a F-connector, USB, DVI and IEEE 1394 connector, and network connectors.

14. The system of claim 13, comprising one or more component retention holders, disposed on the outer surface of the bus routing component, and configured to selectably retain the suction tube and a power cord and one or more of a cord, cable, bus, and tube from a second clinical operation component in selectable engagement with the bus routing component.

15. The system of claim 14, the first part of the clinical operation component comprising a monitoring device, and the second part of the clinical operation component comprising a patient sensor configured to provide data to the monitoring device.

16. A method for manufacturing an apparatus for managing routing of a clinical operation component line, comprising:
 fixedly coupling a first connection port disposed on a first receptacle with a first end of a first communication bus disposed in a flexible sleeve, the first connection port configured to selectably receive a first connector engaged with a first part of a first clinical operation component, the first communication bus selectably engaged with an anesthesia machine;
 fixedly coupling a second connection port disposed on a second receptacle with a second end of the first communication bus, the second connection port configured to selectably receive a second connector engaged with a second part of the first clinical operation component;
 sealably engaging the first receptacle with a first end of the flexible sleeve;
 sealably engaging the second receptacle with a second end of the flexible sleeve; and,
 operably coupling a station engagement component with the second receptacle, the station engagement component configured to selectably engage with a clinical operation station, wherein the clinical operation station being one or more of one or more of:
 a patient bed;
 a clinical table; and
 a patient cart.

17. The method of claim 16, comprising coupling one or more component retention holders on the outer surface of the flexible sleeve, the component retention holders configured to selectably retain one or more of a cord, cable, bus, and tube from a second clinical operation component in engagement with the flexible sleeve.

18. The method of claim 16, comprising:
 fixedly coupling a third connection port, disposed on the first receptacle, with a first end of a second communication bus disposed in the flexible sleeve, the third connection port configured to selectably receive a third connector engaged with a first part of a third clinical operation component; and
 fixedly coupling a fourth connection port, disposed on the second receptacle, with a second end of the second communication bus disposed in the flexible sleeve, the fourth connection port configured to selectably receive a fourth connector engaged with a second part of the third clinical operation component.

* * * * *